US010675707B2

(12) United States Patent
Mitchell et al.

(10) Patent No.: US 10,675,707 B2
(45) Date of Patent: Jun. 9, 2020

(54) METHOD OF MAKING A MEDICAL DEVICE USING ADDITIVE MANUFACTURING

(71) Applicant: Medtronic Vascular, Inc., Santa Rosa, CA (US)

(72) Inventors: James Mitchell, Windsor, CA (US); Syamala Rani Pulugurtha, Irvine, CA (US)

(73) Assignee: Medtronic Vascular, Inc., Santa Rosa, CA (US)

(*) Notice: Subject to any disclaimer, the term of this patent is extended or adjusted under 35 U.S.C. 154(b) by 169 days.

(21) Appl. No.: 15/491,138

(22) Filed: Apr. 19, 2017

(65) Prior Publication Data

US 2018/0303642 A1 Oct. 25, 2018

(51) Int. Cl.
*B23K 26/00* (2014.01)
*B33Y 10/00* (2015.01)
*B33Y 80/00* (2015.01)
*B33Y 70/00* (2020.01)
*B22F 3/105* (2006.01)
(Continued)

(52) U.S. Cl.
CPC .......... *B23K 26/0093* (2013.01); *A61F 2/915* (2013.01); *B22F 3/1055* (2013.01); *B22F 3/24* (2013.01); *B22F 5/106* (2013.01); *B33Y 10/00* (2014.12); *B33Y 70/00* (2014.12); *B33Y 80/00* (2014.12); *A61F 2002/91575* (2013.01); *A61F 2230/0069* (2013.01); *A61F 2240/001* (2013.01); *B22F 2003/1058* (2013.01); *B22F 2998/10* (2013.01); *B23K 2101/04* (2018.08); *B23K 2101/22* (2018.08)

(58) Field of Classification Search
CPC .............................................. B22F 2003/1058
See application file for complete search history.

(56) References Cited

U.S. PATENT DOCUMENTS 6,676,892 B2 * 1/2004 Das ...................... B22F 3/1055
419/7
6,830,643 B1 * 12/2004 Hayes ...................... B41M 3/006
156/241

(Continued)

OTHER PUBLICATIONS

Jhabvala, An innovative method to build support structures with a pulsed laser in the selective laser melting process, 2012, Int J Adv Manuf Technol (2012) 59:137-142 (Year: 2012).*

(Continued)

*Primary Examiner* — Jacob J Cigna
(74) *Attorney, Agent, or Firm* — Medler Ferro Woodhouse & Mills PLLC (57) ABSTRACT

A method of making a medical device includes forming a precursor medical device using additive manufacturing. The precursor medical device includes a first portion, a second portion, a first connector, and a second connector. The first connector connects the first portion to the second portion and is configured to remain. The second connector connects the first portion to the second portion and are configured to be removed. The second connector is formed such that the second connector is less ductile than the first portion, the second portion, and the first connector. The precursor medical device is processed to remove the second connector without adversely affecting the first portion, the second portion, and the first connector.

8 Claims, 6 Drawing Sheets

(51) Int. Cl.
*B22F 3/24* (2006.01)
*B22F 5/10* (2006.01)
*A61F 2/915* (2013.01)
*B23K 101/04* (2006.01)
*B23K 101/22* (2006.01)

(56) References Cited

U.S. PATENT DOCUMENTS

| | | | | |
|---|---|---|---|---|
| 8,052,743 | B2* | 11/2011 | Weber | A61F 2/82 424/426 |
| 8,089,029 | B2* | 1/2012 | Flanagan | B23K 26/40 219/121.7 |
| 8,353,952 | B2 | 1/2013 | Thompson et al. | |
| 8,903,533 | B2* | 12/2014 | Eggers | G06T 17/10 700/119 |
| 9,114,032 | B1* | 8/2015 | Pulugurtha | C23F 1/02 |
| 9,643,281 | B1* | 5/2017 | Memmen | B23K 26/342 |
| 2005/0182479 | A1* | 8/2005 | Bonsignore | A61F 2/91 623/1.15 |
| 2006/0079953 | A1* | 4/2006 | Gregorich | A61F 2/3662 623/1.15 |
| 2006/0122694 | A1* | 6/2006 | Stinson | A61F 2/91 623/1.34 |
| 2007/0061007 | A1 | 3/2007 | Nolting | |
| 2007/0219626 | A1* | 9/2007 | Rolando | A61F 2/91 623/1.16 |
| 2008/0131479 | A1* | 6/2008 | Weber | A61F 2/82 424/426 |
| 2010/0087910 | A1* | 4/2010 | Weber | A61L 31/022 623/1.15 |
| 2010/0228369 | A1* | 9/2010 | Eggers | G06T 17/10 700/98 |
| 2010/0291401 | A1* | 11/2010 | Medina | B23K 15/0086 428/593 |
| 2011/0067778 | A1 | 3/2011 | Mitchell et al. | |
| 2011/0070357 | A1 | 3/2011 | Mitchell et al. | |
| 2012/0067454 | A1 | 3/2012 | Melder | |
| 2012/0067455 | A1 | 3/2012 | Mitchell et al. | |
| 2012/0070562 | A1 | 3/2012 | Avelar et al. | |
| 2012/0070563 | A1 | 3/2012 | Mitchell et al. | |
| 2016/0107234 | A1* | 4/2016 | Craeghs | B28B 1/001 419/53 |
| 2016/0229127 | A1* | 8/2016 | Halliday | B29C 67/0092 |
| 2016/0368054 | A1* | 12/2016 | Ng | B22F 3/1055 |
| 2016/0375490 | A1* | 12/2016 | Marchione | B22F 3/1055 419/55 |
| 2017/0072636 | A1* | 3/2017 | Ng | B29C 64/153 |
| 2017/0189965 | A1* | 7/2017 | Vaidya | B23K 26/0876 |
| 2019/0039137 | A1* | 2/2019 | Hildreth | C04B 35/565 |

OTHER PUBLICATIONS

Barnett, Weak support material techniques for alternative additive manufacturing materials, 2015, Additive Manufacturing 8 (2015) 95-104 (Year: 2015).*

Hussein, Advanced lattice support structures for metal additive manufacturing, Journal of Materials Processing Technology 213 (2013) 1019-1026 (Year: 2013).*

Jhabvala, On the effect of scanning strategies in the selective laser melting process, Virtual and Physical Prototyping • Jun. 2010 (Year: 2010).*

Denney P., et al., "Triple Hopper Powder Feeder System for Variable Composition Laser Cladding", Laser Materials Processing, vol. 77, Oct. 24-28, 1993.

* cited by examiner

METHOD OF MAKING A MEDICAL DEVICE USING ADDITIVE MANUFACTURING

FIELD OF THE INVENTION

The invention relates generally to methods of making a medical device, and more particularly to a method of making stents using rapid form prototyping or additive manufacturing.

BACKGROUND OF THE INVENTION

A wide range of medical treatments exist that utilize medical devices including stents or endoluminal prostheses. As used herein, the term "stent" is intended to cover medical devices that are adapted for temporary or permanent implantation within a body lumen, including both naturally occurring and artificially made lumens, such as without limitation: arteries, whether located within the coronary, mesentery, peripheral, or cerebral vasculature; veins; gastrointestinal tract; biliary tract; urethra; trachea; hepatic shunts; and fallopian tubes.

Accordingly, different stents have been developed, each providing a uniquely beneficial structure to modify the mechanics of the targeted lumen wall. For example, stent prostheses are known for implantation within body lumens to provide artificial radial support to the wall tissue, which forms the various lumens within the body.

Stents have been made by a variety of methods, including forming a wire into waveform and helically wrapping the waveform around a mandrel, removing material from a tubular cylinder such as by a laser to leave a stent (sometimes referred to as a tubular slotted stent or a laser cut stent), and forming individual cylindrical components and attaching adjacent cylindrical components to each other to form a tube. Such methods can be laborious, expensive, and time-consuming. It would be desirable to use additive manufacturing techniques, also known as rapid prototyping methods and three-dimensional printing, to make stents and other medical devices. However, additive manufacturing techniques may be limited in making certain shapes for a medical device, and particularly for certain shapes of stents. For example, and not by way of limitation, certain medical devices that are generally tubular, such as stents, may be formed by additive manufacturing by building the medical device vertically. In other words, the longitudinal axis of the medical device is perpendicular to the surface or substrate upon which the medical device is built. In additive manufacturing, layers of material for the medical device are built upon previous layers of the material. In certain medical devices, such as certain stents, it is desirable for a significant portion of a perimeter of a first portion of the device to not be connected to a second portion of the device. For example, and not by way of limitation, in a stent with a plurality of bands formed from struts and crowns, it is often desirable for only some of the crowns of a band to be connected to crowns of an adjacent band. However, when building such a stent vertically by additive manufacturing as described above, it is desirable for connectors to be built between most or all of the crowns of adjacent bands in order to provide a support for the following layer of material.

In a solution described in U.S. Pat. No. 9,114,032 assigned to Medtronic Vascular, Inc., incorporated by reference herein in its entirety, connectors are formed between crowns of a stent by additive manufacturing. Some of the connectors are then removed by laser removal, chemical etching, or other methods. In particular embodiments, the connectors configured to be removed are formed from a different material than the connectors configured to remain. Then, the precursor stent is exposed to a chemical etchant that dissolves/removes the connectors configured to be removed without adversely affecting the stent components configured to remain. However, changing materials during additive manufacturing may complicate the process. Further, removal by chemical etching is not always desirable. Still further, mechanical removal of connectors may be difficult if the connectors to be removed are the same as the connectors to remain.

Accordingly, it would be desirable to build a medical device such as a stent by additive manufacturing with connectors between portions of the medical device that can be more easily, efficiently, and effectively removed without adversely affecting the remaining medical device.

BRIEF SUMMARY OF THE INVENTION

Embodiments hereof relate to a method of making a medical device using additive manufacturing. The method includes forming a precursor medical device. The precursor medical device comprises a first portion, a second portion, a first connector connecting the first portion to the second portion, and a second connector connecting the first portion to the second portion. The first connector is configured to remain. The second connector is configured to be removed. The second connector is formed such that the second connector is less ductile/more brittle than the first portion, the second portion, and the first connector. The precursor medical device is processed to remove the second connector without adversely affecting the first portion, the second portion, or the first connector. In an embodiment, the medical device is a stent.

Embodiments hereof are directed to methods of making the second connector less ductile/more brittle than the first portion, the second portion, and the first connector. Embodiments for embrittlement include incomplete fusion of particles of the second connector, material selection to form intermetallics in the second connector, material selection to form a ceramic second connector, and selection of materials such that exposure to hydrogen in a heated environment causes the second connector to be less ductile than the first connector.

Embodiments hereof also relate to a precursor medical device including a first portion, a second portion, a first connector connecting the first portion to the second portion, and a second connector connecting the first portion to the second portion. The first connector is configured to remain. The second connector is configured to be removed and is less ductile than the first portion, the second portion, and the first connector. In an embodiment, the precursor medical device is a precursor stent.

BRIEF DESCRIPTION OF DRAWINGS

The foregoing and other features and advantages of the invention will be apparent from the following description of embodiments hereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

DETAILED DESCRIPTION OF THE INVENTION

Specific embodiments of the present invention are now described with reference to the figures, wherein like reference numbers indicate identical or functionally similar elements.

Figure 1:
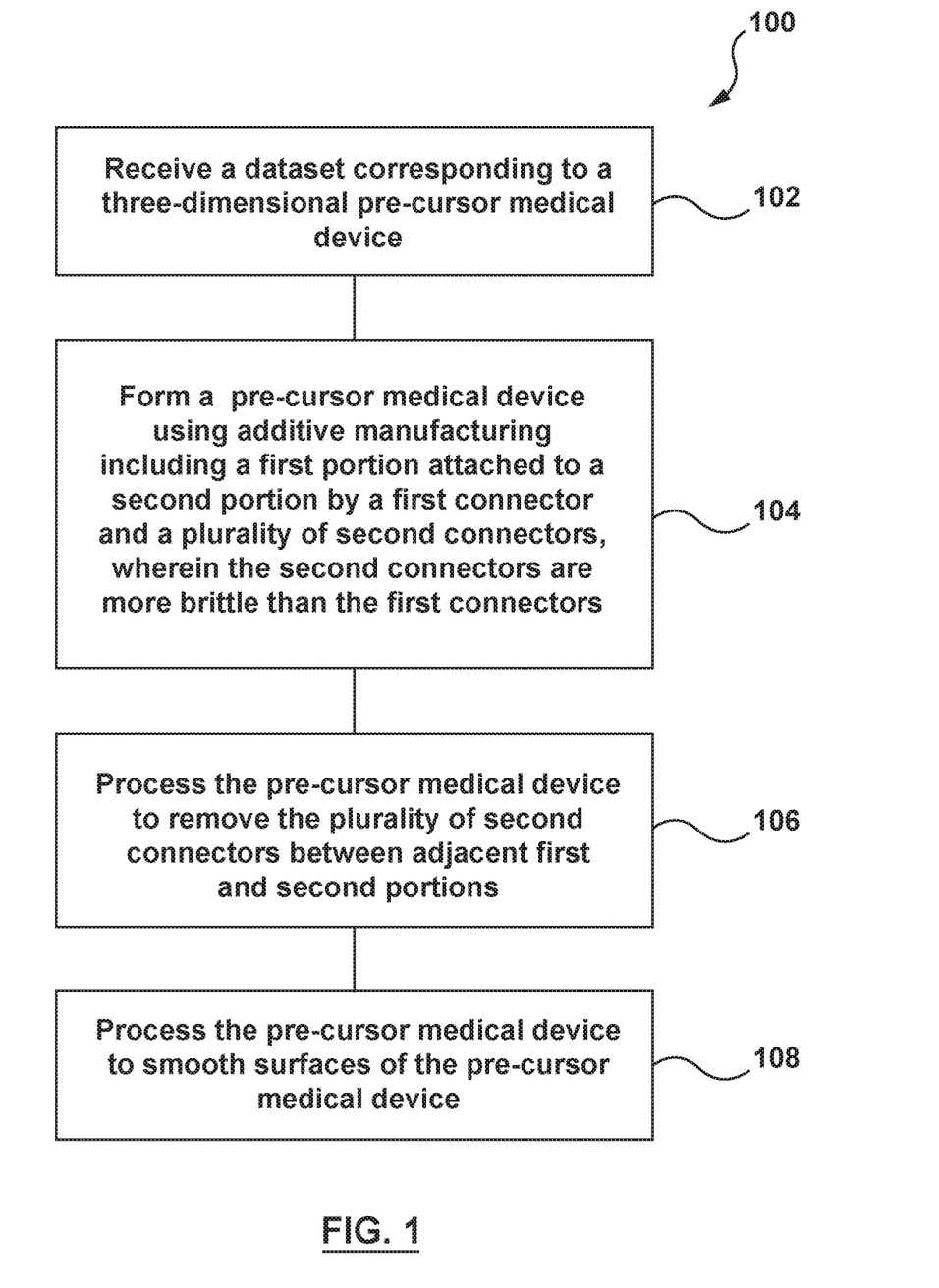
FIG. 1 is a flow chart showing steps in a method of making a medical device according to an embodiment hereof.

FIG. 1 is a flow chart showing an embodiment of a method 100 of forming a medical device. The methods as described with respect to FIG. 1 are methods for making a medical device using "additive manufacturing" or "three-dimensional printing" (3D printing) or "rapid prototyping". The terms "additive manufacturing" or "three-dimensional printing" or "rapid prototyping" refer to a process of making a three-dimensional solid object of virtually any shape from a digital model. 3D printing is achieved using an additive process, where successive layers of material are laid down in different shapes. The terms, as used herein, may refer to methods such as, but not limited to, selective laser melting (SLM), direct metal laser sintering (DMLS), selective laser sintering (SLS), fused deposition modeling (FDM), and stereolithography (SLA). Further, any type of additive manufacturing machine that can print the materials described herein may be used.

Figure 2:
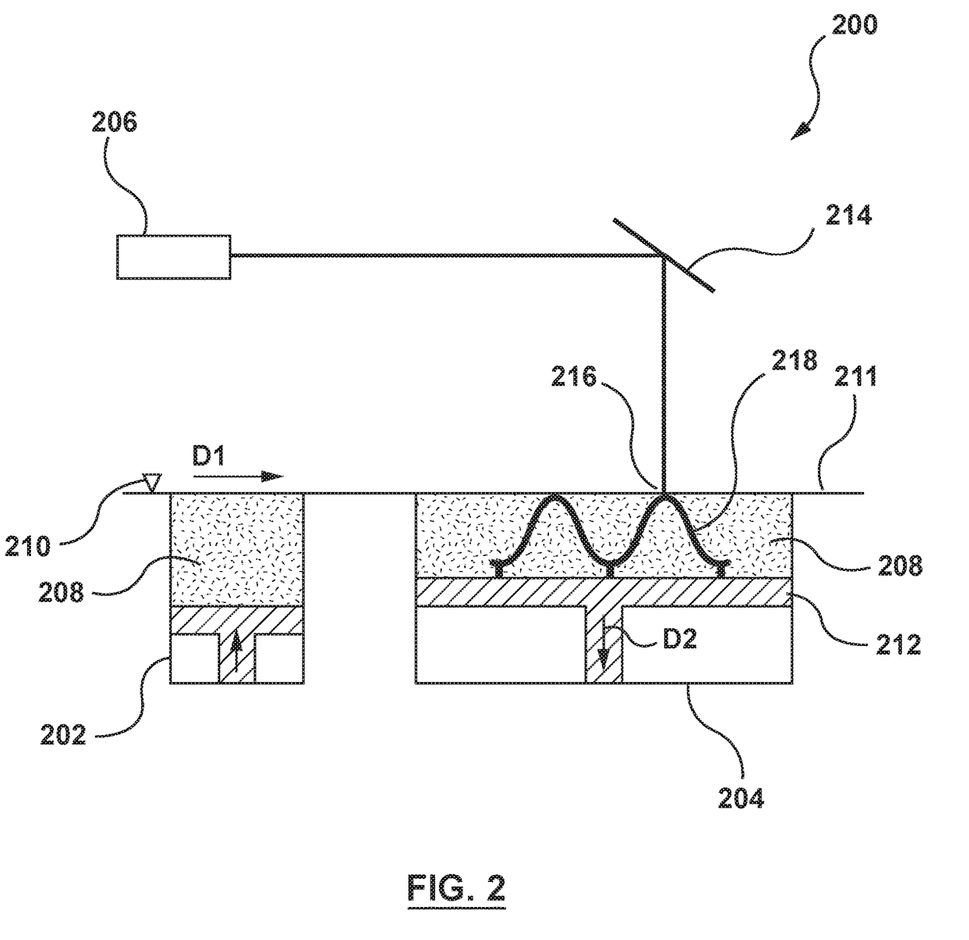
FIG. 2 is a schematic illustration of an embodiment of an additive manufacturing system suitable for use with the method of FIG. 1.

Accordingly, FIG. 2 shows a simplified exemplary embodiment of an additive manufacturing system 200 suitable for the purposes described herein. The additive manufacturing system 200 of FIG. 2 includes a powder delivery system 202, a build space 204, and an energy source 206. In general, a powder material 208 from the powder delivery system 202 is spread by a blade 210 on a surface 211 in a direction D1 such that a thin layer of the powder material 208 is deposited over a substrate 212 of the build space 204. The energy source 206 (such as a laser, electron beam, or similar source) is targeted by a mirror 214 to selectively fuse the powder material 208 at a fusion zone or laser focal zone 216 in a desired pattern. The substrate 212 is retracted in a direction D2 and successive layers of distributed powder material 208 are deposited thereon and selectively fused until the desired object 218 is formed. Thus, while FIG. 2 shows the substrate 212 partially retracted after several layers of the powder material have been fused, the substrate 212 starts the process adjacent the surface 211. Thus, the object 218 (in this embodiment a precursor stent as described below) is built layer-by-layer. However, in order for a subsequent layer of powder material 208 to be fused, it must be supported. Typically, support is provided by the preceding layer of fused material. However, with certain medical devices, such as certain stents, it is desirable for a significant portion of a perimeter of a first band (portion) of the stent to not be connected to a second band (portion) of the stent. However, in many embodiments, these portions cannot be excluding during additive manufacturing because the following layers need support upon which to build. Thus, when building such a stent vertically by additive manufacturing, it may be necessary for connectors to be built between most or all of the crowns of adjacent bands in order to provide a support for the following layer of material. The powder-bed additive manufacturing system 200 of FIG. 2 is provided for exemplary purposes only and not meant to limit the invention. Other additive manufacturing systems are possible including, but not limited to a powder-fed, funnel-fed, or conduit-fed additive manufacturing systems.

The method of FIG. 1 using the additive manufacturing system 200 such as described in FIG. 2 will now be described in more detail. In an embodiment, in step 102 of FIG. 1, the additive manufacturing system 200 receives a dataset corresponding to a medical device such as a precursor stent 300 (shown in FIG. 3). In particular, the dataset is information regarding the characteristics of the precursor stent 300 from which the additive manufacturing system 200 can form the precursor stent 300. For example, the sizes and locations of parts of the precursor stent 300 may be part of the dataset such that the additive manufacturing system 200 can form the precursor stent 300. For example, and not by way of limitation, the dataset may be a 3D printable file such as an STL file. STL (STereoLithography) is a file format native to the stereolithography CAD software created by 3D Systems. STL is also known as Standard Tessellation Language. This file format is supported by many software packages for use in 3D printing.

Figure 3:
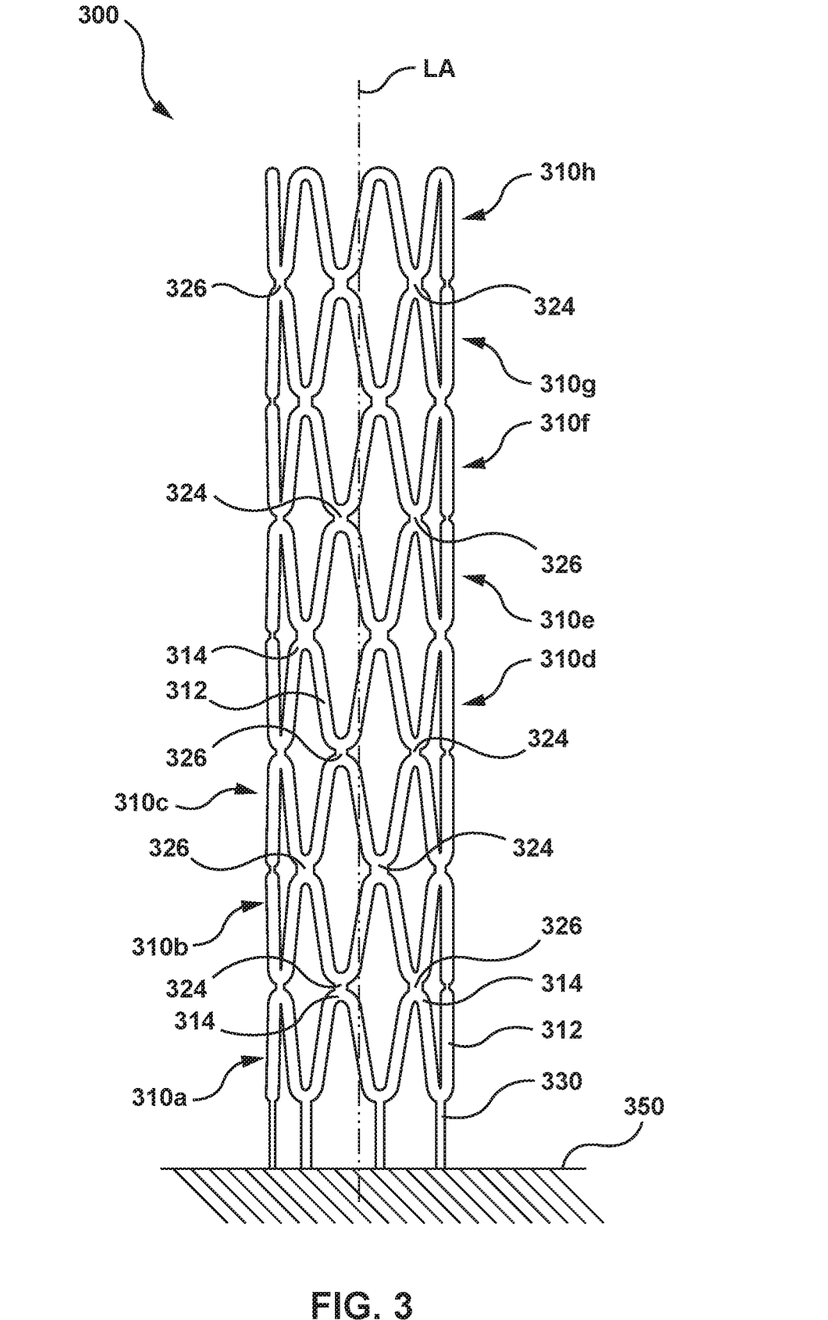
FIG. 3 is a schematic side illustration of an embodiment of a precursor stent made in a step of the method of FIG. 1.

Step 104 of the method of FIG. 1 is for the additive manufacturing system 200 to form the precursor stent 300, as shown in FIG. 3. In step 104, the additive manufacturing system 200 lays down successive layers of a powder of the desired material to build the precursor stent 300 from a series of cross sections. FIG. 3 shows an embodiment of the precursor stent 300. According to an embodiment hereof, the precursor stent 300 is built by additive manufacturing such that the precursor stent 300 is built vertically on the substrate 212. The substrate 212 may be any material suitable to be used in the environment of and with the materials used for the additive manufacturing process. In the embodiment shown, the precursor stent 300 includes a plurality of ring-shaped elements or bands 310. The bands 310 may also be referred to as cylindrical elements or portions of the precursor stent 300. In the embodiment of FIG. 3, the precursor stent 300 includes eight bands 310a-310h; however, more or fewer bands 310 may be utilized. Each band 310 is disposed adjacent to another band 310 along a longitudinal axis LA to form a tube or cylinder. In an embodiment, each band 310 is a waveform formed from a plurality of struts 312 connected together by bends or crowns 314. Further, the crowns 314 of the adjacent bands 310 are connected to each other by at least one first connector 324 and a plurality of second connectors 326. Further, in an embodiment, the first band 310a is separated from the substrate 212 by stilts or connectors 330, as shown in FIG. 3, which may also be built by additive manufacturing.

The first connectors 324 and the second connectors 326 are distinguished from each other in that the first connectors 324 are configured to remain connecting the adjacent crowns 314 to each other and the second connectors 326 are configured to be removable from the precursor stent 300. Similarly, the stilts 330 are configured to be removable from the precursor stent 300 such that the band 310a closest to the substrate 212 is not damaged when separating the precursor stent 300 from the substrate 212. Although a particular precursor stent 300 embodiment is shown in FIG. 3, different precursor stents may be formed using additive manufacturing. For example, and not by way of limitation, additional connectors may be utilized, the bands may be slanted, different bands may have different features (such as different thicknesses), additional features such as surface features, notches, etc. may be added, and other stent design differences may be utilized which are capable of being made using additive manufacturing.

As explained above, each crown 314 of a band 310 is connected to a corresponding crown 314 of an adjacent band 310 by a first connector 324 or a second connector 326. However, as also explained above, for certain applications it would be desirable for some of the crowns 314 of a band 310 to be independent or not connected to the corresponding crown 314 of an adjacent band 310. As also explained above, the second connectors 326 may not be able to be excluded from the precursor stent 300 during the additive manufacturing process because excluding such second connectors 326 when building the precursor stent 300 vertically on the substrate 212 would result in instability between the bands 310. For example, and not by way of limitation, if only one first connector 324 were included between the first band 310a and the second band 310b, the second band 310b would tend to move towards the first band 310a at the crowns 314 without a connector due to gravity. Such a tendency would negatively impact the ability to build a stent with the desired characteristics.

Accordingly, step 106 of the method 100 of FIG. 1 is to process the precursor stent 300 to remove the plurality of second connectors 326 between the crowns 314 of adjacent bands 310, as will be described in more detail below. In this particular embodiment, the second connectors 326 are selected to be removed such that only a single first connector 324 is disposed between each band 310 and its adjacent band 310. However, the number and type of second connectors 326 to be removed can be selected depending on various factors including, but not limited to, the desired flexibility of the resulting stent.

In an embodiment described in U.S. Pat. No. 9,114,032 the connectors configured to be removed may be made from a different material than the connectors configured to remain. The precursor stent is then processed, such as by chemical etching, such that the material of the connectors configured to be removed is removed but the material of the connectors configured to remain and the material of the bands is unharmed. However, switching materials during the additive manufacturing process may not be easy in certain additive manufacturing methods. The above-noted patent also describes some mechanical methods for removing some of the connectors. However, mechanically removing connectors that are constructed in the same manner of connectors configured to be removed may be difficult.

Therefore, in an embodiment of the present application, as shown in step 104 of the method 100 of FIG. 1, the second connectors 326 (and optionally the stilts 330) configured to be removed are constructed such that they are more brittle (less ductile) than the first connectors 324 and the bands 310 of the precursor stent 300. With the second connectors 326 and the stilts 330 more brittle than the first connectors 324 and the bands 310, the second connectors 326 and the stilts 330 are easy to remove by mechanical methods. Accordingly, described below are embodiments of methods to make the second connectors 326 and the stilts 330 of the precursor stent 300 more brittle (less ductile) than the first connectors 324 and the bands 310.

As explained above, in the additive manufacturing process, the powder material 208 is deposited over the substrate 212 and fused by the energy source 206 in the shape of a particular layer of the object 208 being formed. In an embodiment, when forming the bands 310 and the first connectors 324, the particles of the powder material 208 are completely fused. However, when forming second connectors 326 and the stilts 330, the particles of the powder material 208 are incompletely or suboptimally fused. Incomplete fusion of the powder material 208 of the second connectors 326 and the stilts 330 keeps the material particles largely unmelted (intact) with fusion of the particles mostly on the surface. This incomplete or suboptimal fusing of the powder material 208 of the second connectors 326 and the stilts 330 results in the second connectors 326 and the stilts 330 being more brittle than the bands 310 and the first connectors 324.

In an embodiment, when forming the bands 310 and the first connectors 324 (i.e., the portions of the precursor stent 300 configured to remain), a first energy per unit area is applied to the powder material 208 of each layer to completely fuse the particles of the powder material 208 to each other and to adjacent layers. When fusing the powder material 208 of the second connectors 326 and optional stilts 330 (i.e., portions of the precursor stent configured to be removed), however, a second energy per unit area is applied to the powder material of each layer to incompletely or suboptimally fuse the particles of the powder material 208 to each other and to adjacent layers. The second energy per unit area is lower than the first energy per unit area such that the second energy per unit area incompletely or suboptimally fuses the powder material 208 of the second connectors 326 and the stilts 330.

Several methods may be utilized to vary the energy applied to the material layers, either individually or in combination. More specifically, the speed of travel of the energy source, the power of the energy source, the distance of the energy source from the powder material, and the pattern of the energy source over the powder material may be varied to affect the energy per unit area applied to the powder material.

For example, in an embodiment, the energy source is a laser. In order to fuse the powder material 208 together and to the previous layer of material, the beam from the laser is moved over the powder material 208 in a pattern, thereby moving the laser focal zone 216 (see FIG. 2). In an embodiment, the laser beam travels faster when fusing the powder material 208 of the layers of the second connectors 326 and the stilts 330 than when fusing the powder material 208 of the layers of the bands 310 and the first connectors 324. In other words, the laser beam spends less time per unit area fusing the layers of second connectors 326 and the stilts 330 than fusing the layers of the bands 310 and the first connectors 324. With the power, distance from the powder material, and patterns of the energy source constant, the faster the rate of travel along the pattern, the less time is spent per unit area. Thus, less energy is applied per unit area. As a result, the laser beam will be applied for less time per unit area to form the plurality of second connectors 326 and the stilts 330 than to form the first connectors 324 and the bands 310 such that the powder material 208 of the layers of the second connectors 326 and the stilts are incompletely or suboptimally fused.

In another embodiment, the energy source includes a first power for the first energy and a second power for the second energy. The second power is lower than the first power. The first power is utilized when the powder material 208 of the layers of the bands 310 and the first connectors 324 are being fused. The second power is utilized when the powder material 208 of the layers of the second connectors 326 and the stilts 330 are being fused. Thus, with the rate of travel of the energy source over the powder material, the distance from the energy source to the powder material 208, and the pattern of travel of the energy source over the powder material all constant, the energy source will apply less energy per unit area to form the second connectors 326 and the stilts 330 than to form the first connectors 324 and the bands 310. The second power is selected such that the energy per unit area applied to the powder material 208 to form the second connectors 326 and the stilts 330 results in incomplete or suboptimal fusion of the powder material.

In another embodiment, the energy source is positioned a first distance from the powder material 208 when applying energy to fuse the first connectors 324 and the bands 310 and a second distance from the powder material 208 when applying energy to fuse the second connectors 326 and the stilts 330. The second distance is greater than the first distance. Thus, with the rate of travel of the energy source across the powder material, the power of the energy source, and the pattern of travel of the energy source over the powder material all constant, the energy source will apply less energy per unit area at the second distance to form the second connectors 326 and the stilts 330 than to form the first connector 324 and the bands 310. The second distance is selected such that the energy per unit area applied to the powder material 208 to form the second connectors 326 and the stilts 330 results in incomplete or suboptimal fusion of the powder material 208.

Figure 4:
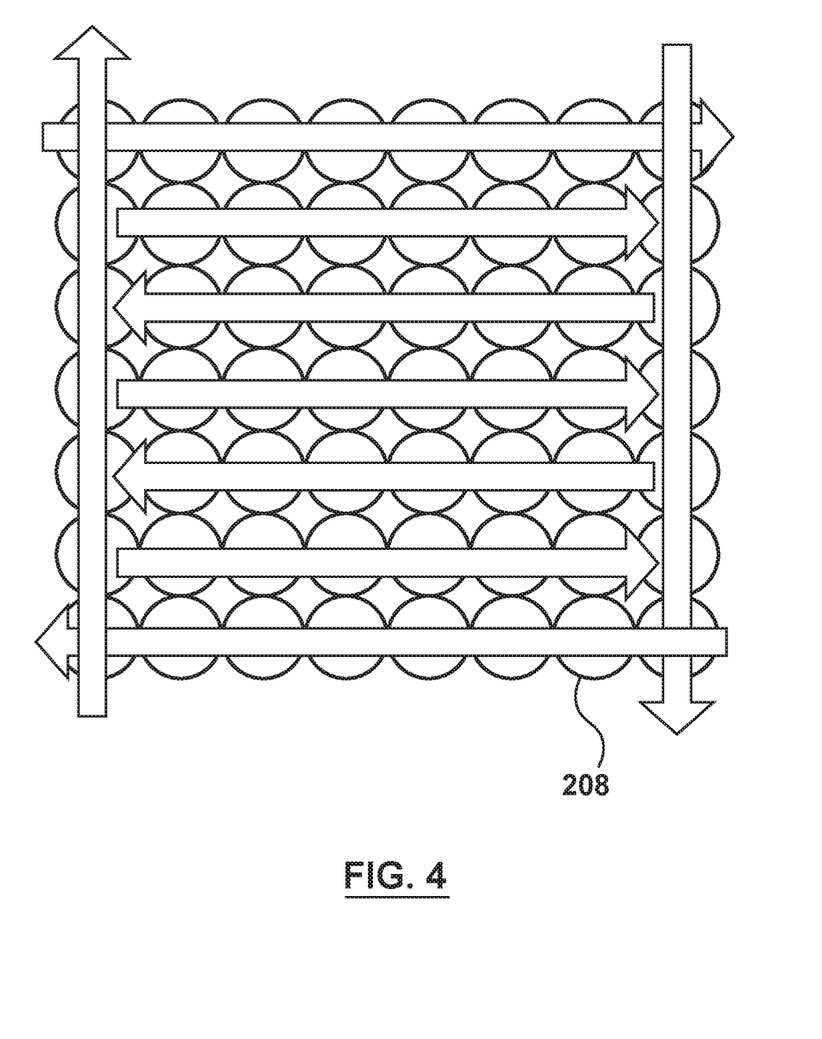
FIG. 4 is an illustration of a first pattern of an energy source completely fusing a layer of powder material.
Figure 5:
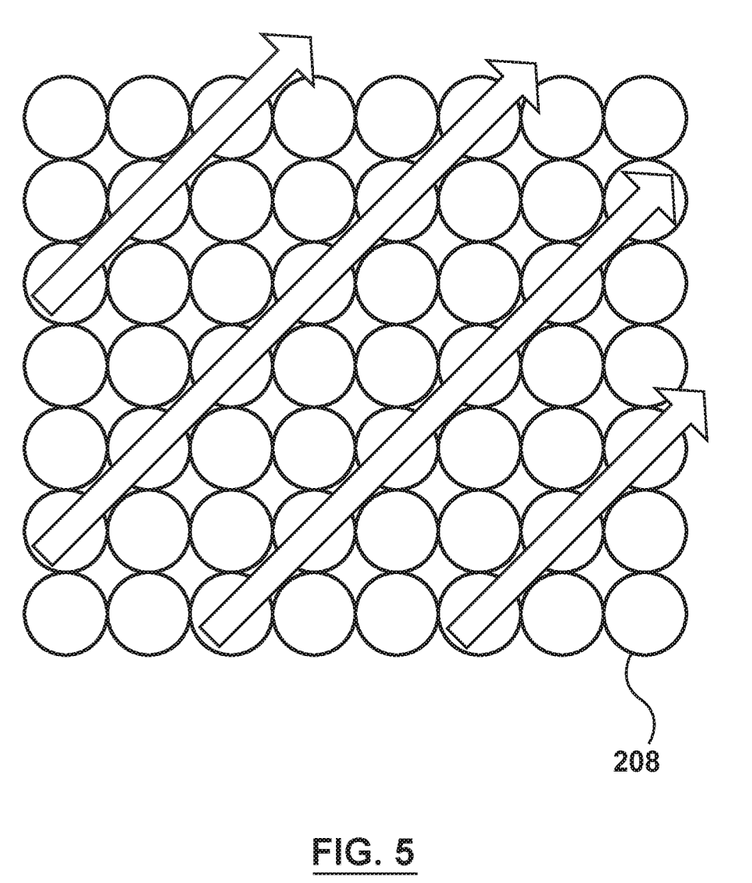
FIG. 5 is an illustration of a second pattern of an energy source incompletely fusing a layer of powder material.

In another embodiment shown in FIGS. 4-5, the energy source travels along a first pattern, indicated by the arrows in FIG. 4, over the particles of the powder material 208 for forming the bands 310 and the first connectors 324. The energy source travels along a second pattern, indicated by the arrows in FIG. 5, over the particles of the powder material 208 for forming the second connectors 326 and the stilts 330. As can be seen comparing FIGS. 4 and 5, the energy source travels over a smaller quantity of the powder material 208 of the location of interest in the second pattern (FIG. 5) than in the first pattern (FIG. 4). Therefore, with the rate of travel, power, and distance from the powder material 208 of the energy source all constant, the energy source applies less energy per unit area to the powder material 208 in the second pattern when forming the second connectors 326 and the stilts 330 than in the first pattern when forming the first connectors 324 and the bands 310. The second pattern is selected such that the energy per unit area applied to the powder material 208 to form the second connectors 326 and the stilts 330 results in incomplete or suboptimal fusion of the powder material 208.

In the embodiments described above regarding incomplete or suboptimal fusion of the second connectors 326 and the stilts 330, the powder material 208 for the second connectors 326 and the stilts 330 may be the same as the powder material 208 for the bands 310 and the first connectors 324. This may simplify the additive manufacturing process by not requiring a change in materials for different parts for the precursor stent 300. The powder material 208 used to form the precursor stent 300 is the material desired from the finished stent 400 (FIG. 6) described in more detail below. Examples of powder materials which may be used in additive manufacturing to form the precursor stent 300 include, but are not limited to, stainless steel (e.g., 316SS), cobalt-chromium alloys, nickel titanium alloys such as Nitinol, magnesium and magnesium alloys, or combinations thereof. The term "cobalt-chromium" alloys as used herein includes alloys with cobalt and chromium. Generally, materials such as, but not limited to, cobalt-nickel-chromium alloys ("MP35N", "MP20N", and "MP35N LT") and chromium-nickel-tungsten-cobalt alloys ("L605") and cobalt-chromium-nickel-molybdenum alloys ("ELGILOY") are the types of materials included in the term "cobalt-chromium alloys" as used herein.

In another embodiment, in step 104 of the method of FIG. 1, the plurality of second connectors 326 and the stilts 330 are made less ductile/more brittle than the first connectors 324 and the bands 310 by forming the second connectors 326 and the stilts 330 by mixing different materials that will form intermetallics. In particular, at the location of the second connectors 326, two different materials are mixed as the powder material 208. These two different materials are selected such that when they are fused, intermetallics are formed which are more brittle than the fused particles used to form the first connectors 324 and the bands 310. Preferably, the mixture of particles for the second connectors 326 and the stilts 330 includes the same material as the material used to form the first connectors 324 and the bands 310, and a second, different material.

For example, in an embodiment, stainless steel alloy particles (e.g., 316SS) are used to form the bands 310 and the first connectors 324. In the locations of the second connectors 326 and the stilts 330, a mixture of the stainless steel particles and aluminum particles is used. When the mixture of stainless steel particles and aluminum particles is fused, the resulting fused material is more brittle than when stainless steel particles alone are fused. Thus, the second connectors 326 and the stilts 330 will be more brittle than the first connectors 324 and the bands 310. The chart below shows other examples of materials that can be used to form intermetallics at the location of the second connectors 326 and the stilts 330. These example materials are associated with the "Embrittlement Process" labeled "Intermetallics" in the chart.

In another embodiment, the second connectors 326 and the stilts 330 may be made from a ceramic material formed when the particles of the powder material are fused, while the first connectors 324 and the bands 310 are made from materials commonly used for stents, such as but not limited to 316SS, MP35N, NiTi, or L605. For example, and not by way of limitation, the second connectors 326 and the stilts 330 may be made from aluminum oxide particles that when fused by the energy source form a ceramic material which is low in ductility (i.e. brittle). The chart below shows other examples of materials that can be used to form brittle ceramics at the location of the second connectors 326 and the stilts 330. These example materials are associated with the "Embrittlement Process" labeled "Ceramics" in the chart.

In another embodiment, the second connectors 326 and the stilts 330 may be made from a material that is more susceptible to hydrogen embrittlement than the material used to make the first connectors 324 and the bands 310. For example, and not by way of limitation, the second connectors 326 and the stilts 330 may be formed from tantalum, while the first connectors 324 and the bands 310 are formed from stainless steel (e.g., 316SS). The precursor stent 300 is exposed to hydrogen gas in a heated environment. The exposure forms detrimental hydrides in the tantalum, decreasing ductility of the second connectors 326 and the stilts 330. The chart below shows other examples of materials that can be used at the location of the second connectors 326 and the stilts 330 such that when exposed to hydrogen gas in a heated environment, the second connectors 326 and the stilts 330 become less ductile/more brittle than the first connectors 324 and the bands 310. These example materials are associated with the "Embrittlement Process" labeled "Hydrogen Exposure" in the chart.

| Embrittlement Process | bands 310/ first connectors 324 | second connectors 326/ stilts 330 |
|---|---|---|
| Intermetallics | 316SS, MP35N, NiTi, or L605 | Mixture of material for the Bands 310/connectors 324 and Aluminum, Magnesium, Copper, Zinc, Titanium, or Tantalum |
| Ceramics | 316SS, MP35N, NiTi, or L605 | Aluminum Oxide, Calcium Carbonate, Hydroxyapatite, Silicon Carbide, or Zirconium dioxide |
| Hydrogen Exposure | 316SS, MP35N, or L605 | Magnesium, Tantalum, or Titanium |

In the examples above, different materials are used for the portions of the precursor stent 300 configured to remain (the first connectors 324 and the bands 310) and the portions of the precursor stent configured to be removed (the second connectors 326 and the stilts 310). To change materials for different portions of the precursor stent 300, instead of using a powder bed with the blade 210 spreading material, as shown in FIG. 2, a multiple hopper system may be used. For example, in the intermetallics example above, a first hopper may include a first material of the bands 310 and the first connectors 324, and a second hopper may include a second material to be mixed with the first material to form the second connectors 326 and the stilts 330. When forming the bands 310 and the connectors 324, the first material from the first hopper is dispensed to be fused by the energy source. When forming the second connectors 326 and the stilts 310, the first material from the first hopper and the second material from the second hopper are both dispensed to a mixer and then to the bed to be fused by the energy source. A lesser amount of the first material is dispensed when forming the second connectors 326 and the stilts 330 than when forming the bands 310 and the connectors 324 due to the addition of the second material. In another option, the first hopper may include the first material and the second hopper may include a mixture of the first material and the second material. When forming the bands 310 and the first connectors 324, the first material from the first hopper is dispensed. When forming the second connectors 326 and the stilts 330 the mixture of the first material and the second material from the second hopper is dispensed. Similarly, in the "ceramics" and "hydrogen exposure", a first material for the first connectors 324 and the bands 310 may be dispensed from a first hoper, and a second material for the second connectors 326 and the stilts 330 may be dispensed from a second hopper. An example of a multiple hopper system can be seen in Sexton et al., "Triple Hopper Powder Feeder System for Variable Composition Laser Cladding", *Proceedings of SPIE—The International Society for Optical Engineering*, January 1994, pages 824-834, which is incorporated by reference herein in its entirety.

Thus, as explained in detail above, step 104 of the method 100 for forming a precursor stent 300 by additive manufacturing includes forming the second connectors 326 and the stilts 330 such that the second connectors 326 and the stilts 330 are less ductile (more brittle) than the bands 310 and the first connectors 324. Several methods of forming the second connectors 326 and the stilts 330 such that they are more brittle than the first connectors 324 and the bands 310 are disclosed above. Further, when using the terms "more brittle" or "less brittle" or "more ductile" or "less ductile", it is meant that the parts discussed are "more brittle" or "less ductile" per unit volume of the part.

With the precursor stent 300 made, step 106 of the method of FIG. 1 is to remove the second connectors 326 and the stilts 330 without damaging the bands 310 and the first connectors 324. As explained above, the second connectors 326 and the stilts 330 are more brittle than the first connectors 324 and the bands 310. Thus, the second connectors 326 and the stilts 330 are more easily removed by mechanical methods than if they were more ductile like the first connectors 324 and the bands 310. The second connectors 326 and the stilts 330 may be removed by mechanical methods such as, but not limited to, laser ablation, electrical discharge machining (EDM), water jet, electron beam, focused ion beam (FIB), micromachining, and other similar mechanical methods. Further, in an embodiment, as explained in U.S. Pat. No. 9,114,032, the dataset used for the additive manufacturing system to build the precursor stent 300 may also provide information to assist in removing the second connectors 326.

FIG. 1 also shows an optional step 108 of processing the precursor stent 300 to smooth surfaces of the precursor stent 300. In some additive manufacturing processes, the objects are formed with coarse surfaces, burrs, and residue powder that are not sufficiently smooth for use as certain medical device, such as stents. Accordingly, step 108 may be electropolishing, laser micro-machining, or other processes to smooth the surfaces of the precursor stent 300. Accordingly, the struts 312 and the crowns 314 of the bands 310, and the first connectors 324, of the precursor stent 300 may be slightly thicker than the final desired thickness of these elements to account for processes to smooth or otherwise finish the precursor stent 300 since such processes may be subtractive processes. Other finishing processes may be performed on the precursor stent 300 to prepare the precursor stent 300 for use in a body, such as, but not limited to, passivation and sterilization. Further processing may also include steps such as adding coatings to the stent, adding radiopaque markers, adding biologically or pharmaceutically active substances to the stent, and/or adding surface features (such as recesses) to the stent. Some of this described further processing may instead be included in step 104 of forming the precursor stent. For example, and not by way of limitation, surface features such as recesses may be formed in the stent as part of the additive manufacturing process. Step 108 may be performed before or after step 106.

Figure 6:
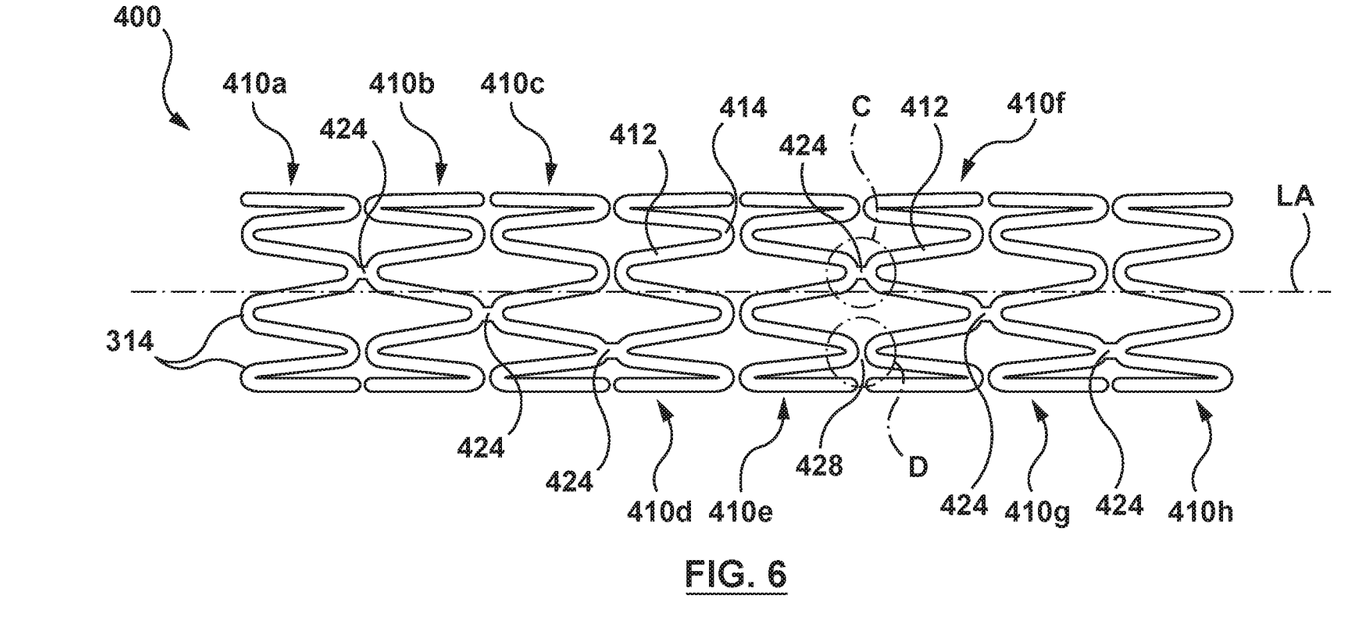
FIG. 6 is schematic side illustration of an embodiment of a stent made using the method of FIG. 1.
Figure 7:
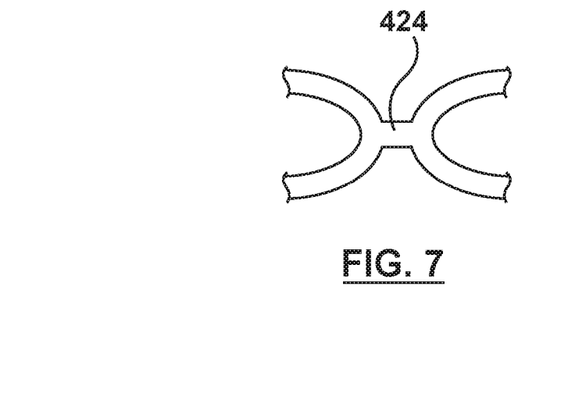
FIG. 7 is a close-up schematic illustration of an embodiment of a first connector between crowns of adjacent bands of the stent of FIG. 6 taken at area "C" of FIG. 6.
Figure 8:
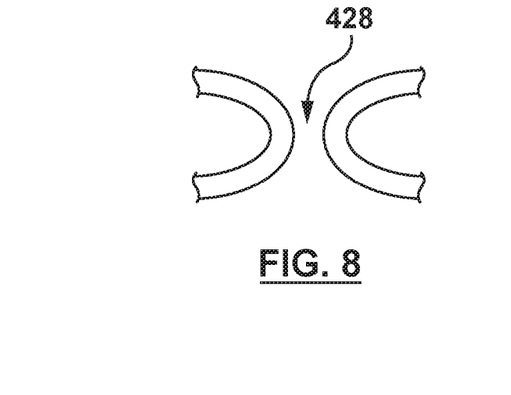
FIG. 8 is a close-up schematic illustration of an embodiment of a gap between crowns of adjacent bands of the stent of FIG. 6 taken at area "D" of FIG. 6.

With method 100 completed and the second connectors 326 and the stilts 330 removed, the precursor stent 300 has been transformed to the stent 400 shown in FIGS. 6-8. The stent 400 includes a plurality of ring-shaped elements or portions or cylindrical elements or bands 410. In the embodiment of FIG. 6, the stent 400 includes eight bands 410a-410h corresponding to the eight bands 310a-310h of the precursor stent 300. However, more or fewer bands 410 may be utilized. Each band 410 is disposed adjacent to another band 410 along a longitudinal axis LA to form a tube or cylinder. Each band 410 is a waveform formed from a plurality of struts 412 connected together by bends or crowns 414. At least one crown 414 of each band 410 is connected to a corresponding crown 414 of an adjacent band 410 by a first connector 324. FIG. 7 shows a close-up illustration of one first connector 424 connecting the crowns 414 of adjacent bands 410 to each other. At other crowns 414, a gap 428 is disposed between the crown 414 and the corresponding crown 414 of the adjacent bands 410, as shown in FIG. 8.

Although the embodiments shown and described herein refer to a crown connected to a corresponding crown of an adjacent band on the precursor stent, other connections between adjacent bands may be used instead. For example, and not by way of limitation, a crown of one band may be connected to a strut of an adjacent band, or struts of adjacent bands may be connected. Further, the first connectors 324 and the second connectors 326 may be angled with respect to the longitudinal axis LA or may be curved.

Although the embodiments shown and described herein refer to a precursor stent with bands, a first connector, and a plurality of second connectors, the precursor stent processed to form a stent, this is not meant to limit the method, and other medical devices may be manufactured utilizing the method described herein. More specifically, a precursor medical device may include a first portion coupled to a second portion by a first connector and a plurality of second connectors, the precursor medical device processed to form a medical device.

While various embodiments according to the present invention have been described above, it should be understood that they have been presented by way of illustration and example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:

1. A method making a medical device using additive manufacturing comprising the steps of:
    successively fusing particles of material in layers to form a first portion, a second portion, and at least one first connector of a precursor medical device by applying energy from an energy source a first distance from the particles of material;
    successively incompletely fusing the particles of material in layers to form a plurality of second connectors connecting the first portion to the second portion by applying energy from the energy source at a second distance from the particles of material greater than the first distance; and
    processing the precursor medical device to remove the plurality of second connectors without adversely affecting the first portion, the second portion, and the at least one first connector.

2. The method of claim 1, wherein the step of processing the precursor medical device is selected from the group consisting of laser ablation, electric discharge machines, water jet, electron beam, focused ion beam, and micromachining.

3. The method of claim 1,
    wherein the medical device is a stent and the precursor medical device is a precursor stent, and
    wherein the first portion is a first band and the second portion is a second band, wherein the first band and the second band each includes a plurality of struts connected by a plurality of crowns, and wherein each crown of each band is attached to a corresponding crown of an adjacent band by one of the at least one first connector configured to remain or by one of the plurality of second connectors configured to be removed.

4. The method of claim 1, wherein the energy source is a laser.

5. A method making a medical device using additive manufacturing comprising the steps of:
    successively fusing particles of a first powder material in layers to form a first portion, a second portion, and at least one first connector of a precursor medical device;
    successively fusing particles of a second powder material different than the first powder material in layers to form a plurality of second connectors connecting the first portion to the second portion, wherein the second powder material is selected to create a ceramic material when fused such that the second connectors are less ductile than the first portion, the second portion, and the at least one first connector; and
    processing the precursor medical device to remove the plurality of second connectors without adversely affecting the first portion, the second portion, and the at least one first connector.

6. The method of claim 5, wherein the step of processing the precursor medical device is selected from the group consisting of laser ablation, electric discharge machines, water jet, electron beam, focused ion beam, and micromachining.

7. The method of claim 5,
    wherein the medical device is a stent and the precursor medical device is a precursor stent, and
    wherein the first portion is a first band and the second portion is a second band, wherein the first band and the second band each includes a plurality of struts connected by a plurality of crowns, and wherein each crown of each band is attached to a corresponding crown of an adjacent band by one of the at least one first connector configured to remain or by one of the plurality of second connectors configured to be removed.

8. The method of claim 5, wherein the first powder material is selected from the group consisting of stainless steel, cobalt-chromium alloys, nickel titanium alloys, and chromium-nickel-tungsten-cobalt alloys, and wherein the second powder material is selected from the group consisting of aluminum oxide, calcium carbonate, hydroxyapatite, silicon carbide, and zirconium dioxide.

\* \* \* \* \*